United States Patent
Guvendiren et al.

(10) Patent No.: US 11,491,702 B2
(45) Date of Patent: Nov. 8, 2022

(54) ADDITIVE MANUFACTURING OF CHANNELS

(71) Applicant: New Jersey Institute of Technology, Newark, NJ (US)

(72) Inventors: Murat Guvendiren, Metuchen, NJ (US); Shen Ji, Kearny, NJ (US)

(73) Assignee: New Jersey Institute of Technology, Newark, NJ (US)

(*) Notice: Subject to any disclaimer, the term of this patent is extended or adjusted under 35 U.S.C. 154(b) by 440 days.

(21) Appl. No.: 16/533,216

(22) Filed: Aug. 6, 2019

(65) Prior Publication Data

US 2020/0047399 A1 Feb. 13, 2020

Related U.S. Application Data

(60) Provisional application No. 62/715,869, filed on Aug. 8, 2018.

(51) Int. Cl.
| | |
|---|---|
| *B29C 64/106* | (2017.01) |
| *B29C 64/40* | (2017.01) |
| *A61L 27/52* | (2006.01) |
| *A61L 27/50* | (2006.01) |
| *B33Y 70/00* | (2020.01) |

(Continued)

(52) U.S. Cl.
CPC .......... *B29C 64/106* (2017.08); *A61L 27/507* (2013.01); *A61L 27/52* (2013.01); *B29C 64/40* (2017.08); *B33Y 10/00* (2014.12); *B33Y 70/00* (2014.12); *B33Y 80/00* (2014.12)

(58) Field of Classification Search
None
See application file for complete search history.

(56) References Cited

U.S. PATENT DOCUMENTS

| | | |
|---|---|---|
| 7,766,641 B2 | 8/2010 | Silverbrook |
| 10,759,107 B2 * | 9/2020 | Batchelder .......... B29C 48/0022 |

(Continued)

FOREIGN PATENT DOCUMENTS

| | | | | |
|---|---|---|---|---|
| CN | 107998449 | * | 5/2018 | |
| WO | WO-2010048281 A | * | 4/2010 | ........... A61L 31/129 |

(Continued)

OTHER PUBLICATIONS

Ji S, Guvendiren M. Recent advances in bioink design for 3D bioprinting of tissues and organs. Frontiers in bioengineering and biotechnology. Apr. 5, 2017;5:23.

(Continued)

*Primary Examiner* — Timothy Kennedy
*Assistant Examiner* — Guy F Mongelli
(74) *Attorney, Agent, or Firm* — Lerner, David, Littenberg, Krumholz & Mentlik, LLP

(57) ABSTRACT

A method is disclosed for 3D printing of soft polymeric material such as a hydrogel or elastomer for scaffolds or devices with embedded channels with tunable shape and size such as a channel inner diameter). The method utilizes extrusion based printing of polymer solutions usually referred as direct ink writing (DIW) or BioPlotting, and requires sequential printing of a photocurable polymer solution, herein, referred as the matrix material, and a sacrificial polymer solution that may dissolve in an aqueous media.

16 Claims, 3 Drawing Sheets

(51) Int. Cl.
 *B33Y 10/00* (2015.01)
 *B33Y 80/00* (2015.01)

(56) References Cited

U.S. PATENT DOCUMENTS

| | | | | |
|---|---|---|---|---|
| 2003/0099737 | A1* | 5/2003 | Eldridge | H01R 13/2407 425/385 |
| 2004/0237822 | A1* | 12/2004 | Boland | B01L 3/0268 101/483 |
| 2006/0237880 | A1* | 10/2006 | Wicker | B33Y 70/00 264/401 |
| 2010/0092796 | A1* | 4/2010 | Cao | B29C 59/022 428/600 |
| 2015/0024169 | A1* | 1/2015 | Martin | G03G 15/1625 428/172 |
| 2015/0037445 | A1* | 2/2015 | Murphy | B41J 3/407 425/131.1 |
| 2015/0084232 | A1* | 3/2015 | Rutz | A61L 27/38 264/211.24 |
| 2015/0202348 | A1* | 7/2015 | Dvir | A61L 27/52 424/572 |
| 2016/0167312 | A1 | 6/2016 | Feinberg et al. | |
| 2017/0197371 | A1* | 7/2017 | Fetfatsidis | B29C 64/386 |
| 2017/0198275 | A1* | 7/2017 | Lee | G01N 33/5005 |
| 2017/0218228 | A1* | 8/2017 | Jose | B33Y 80/00 |
| 2018/0104895 | A1* | 4/2018 | Slaczka | B29C 33/3835 |
| 2018/0243988 | A1* | 8/2018 | Lewicki | B33Y 50/02 |
| 2018/0304361 | A1* | 10/2018 | Gibson | B22F 5/10 |

FOREIGN PATENT DOCUMENTS

| | | | | |
|---|---|---|---|---|
| WO | WO-2010048281 | A1* | 4/2010 | A61L 27/48 |
| WO | WO-2018112480 | A1* | 6/2018 | A61L 27/3813 |

OTHER PUBLICATIONS

Murphy SV, Atala A. 3D bioprinting of tissues and organs. Nature biotechnology. Aug. 2014;32(8):773-85.

Miller JS, Stevens KR, Yang MT, Baker BM, Nguyen DH, Cohen DM, Toro E, Chen AA, Galie PA, Yu X, Chaturvedi R. Rapid casting of patterned vascular networks for perfusable engineered three-dimensional tissues. Nature materials. Sep. 2012;11(9):768-74.

Kolesky DB, Truby RL, Gladman AS, Busbee TA, Homan KA, Lewis JA. 3D bioprinting of vascularized, heterogeneous cell-laden tissue constructs. Advanced materials. May 2014;26(19):3124-30.

Liaw CY, Guvendiren M. Current and emerging applications of 3D printing in medicine. Biofabrication. Jun. 7, 2017;9(2):024102.

Wu W, DeConinck A, Lewis JA. Omnidirectional printing of 3D microvascular networks. Advanced materials. Jun. 24, 2011;23(24):H178-83.

Hinton TJ, Jallerat Q, Palchesko RN, Park JH, Grodzicki MS, Shue HJ, Ramadan MH, Hudson AR, Feinberg AW. Three-dimensional printing of complex biological structures by freeform reversible embedding of suspended hydrogels. Science advances. Oct. 1, 2015;1(9):e1500758.

O'Bryan CS, Bhattacharjee T, Hart S, Kabb CP, Schulze KD, Chilakala I, Sumerlin BS, Sawyer WG, Angelini TE. Self-assembled micro-organogels for 3D printing silicone structures. Science advances. May 1, 2017;3(5):e1602800.

Highley CB, Rodell CB, Burdick JA. Direct 3D printing of shear-thinning hydrogels into self-healing hydrogels. Advanced Materials. Sep. 2015;27(34):5075-9.

Kolesky DB, Homan KA, Skylar-Scott MA, Lewis JA. Three-dimensional bioprinting of thick vascularized tissues. Proceedings of the national academy of sciences. Mar. 22, 2016;113(12):3179-84.

Jia W, Gungor-Ozkerim PS, Zhang YS, Yue K, Zhu K, Liu W, Pi Q, Byambaa B, Dokmeci MR, Shin SR, Khademhosseini A. Direct 3D bioprinting of perfusable vascular constructs using a blend bioink. Biomaterials. Nov. 1, 2016;106:58-68.

Hinton TJ, Hudson A, Pusch K, Lee A, Feinberg AW. 3D printing PDMS elastomer in a hydrophilic support bath via freeform reversible embedding. ACS biomaterials science & engineering. Oct. 10, 2016;2(10):1781-6.

Hasany, Masoud et al., "Synthesis, properties, and biomedical applications of alginate methacrylate (ALMA)-based hydrogels: Current advances and challenges," Applied MaterialsToday 24 ( Sep. 2021): 101150. 20 pgs.

* cited by examiner

ADDITIVE MANUFACTURING OF CHANNELS

CROSS-REFERENCE TO RELATED APPLICATION

The present application claims the benefit of the filing date of U.S. Provisional Patent Application No. 62/715,869, filed Aug. 8, 2018, the disclosure of which is hereby incorporated by reference.

FIELD OF THE DISCLOSURE

The present disclosure relates to 3D printing. In particular, the present disclosure relates to additive manufacturing of 3D scaffolds and devices with embedded channels for vasculature.

BACKGROUND

Bioink refers generally to materials composed of living cells that can be used for 3D printing of complex tissue models. Bioinks are materials that mimic an extracellular matrix environment to support high cell viability and potentially to support the adhesion, proliferation, and differentiation of living cells.

Additive manufacturing, commonly known as 3D printing, has become increasingly popular over recent years. Additive manufacturing refers generally to processes used to manufacture a three-dimensional object in which successive layers of material are formed under computer control to create a 3D construct or a device.

One application of additive manufacturing allows fabrication of complex 3D structures from a patient's own medical image, which is not possible with conventional fabrication techniques. Additive manufacturing of biological materials, i.e., bioinks (cells, cell-laden hydrogels, extracellular matrix materials, and their various combinations), is referred as bioprinting. Single extrusion-based bioprinting is one of the mostly utilized 3D printing approaches for tissue and organ printing studies. Recent focus in the biomanufacturing field is to fabricate 3D tissue and organ mimetics, such as in the form of organ-on-a-chip devices, for disease modeling and drug development and screening, to human-scale scaffolds for tissue regeneration.

One of the main bottle necks and problems related to 3D printing for this application of bioprinting is forming channels within soft polymeric materials, such as hydrogels and elastomers. These channels are crucial for organ-on-a-chip devices, tissue/disease models and human-scale scaffolds/tissue mimetics for perfusion of required soluble components as well as development of vascularization.

Recent advances in 3D bioprinting allow development of several printing methods to overcome this problem, but have been met with limited success. These methods include gel-casting, free-form printing, and coaxial printing.

In one method, a sacrificial polymer ink is 3D printed inside a mold, which is then filled with the matrix hydrogel or elastomer, and followed by a crosslinking process. The 3D printed sacrificial structure is usually made of water soluble polymers or hydrogels, such as sugar-based polymers or Pluronic F-127, or other sol-gel transition gel, such as agarose. The sacrificial structure is then dissolved leaving interconnected channels within the hydrogel matrix. In this technique, it is almost impossible to form individual channels spatially distributed within the hydrogel.

A second method requires a bath of support material, which allows 3D printing of another ink within the support material. This limits the available support systems as they should allow a needle to move freely within the support material. Support material is usually a highly viscous polymer solution, a shear thinning hydrogel, or micro size particle/hydrogel suspension.

For free-form printing, there are mainly three approaches. In a first approach, the support material within the bath is a sacrificial material, and matrix material, usually a curable hydrogel solution, is printed inside this sacrificial material followed by the removal of the sacrificial material. For instance, an alginate hydrogel can be printed in a $CaCl_2$-containing gelatin reservoir at room temperature. After the printing process, the whole reservoir, including the printed structure, was heated to 37° C. to gradually melt the gelatin support. A second approach utilizes self-healing hydrogels and sacrificial hydrogels, which enables either printing a sacrificial hydrogel into the self-healing hydrogel followed by the removal of the sacrificial hydrogel. A third free-form approach utilizes digital-light-processing (DLP) printing technology, which requires a laser to spatially cure a photo-curable polymer solution within a reservoir.

It is still a challenge to create vascularized scaffolds or hydrogels with embedded channels for vascularization and soft microfluidic devices from elastomers or hydrogels in a single step. This requires a fast and simple approach to create channels within soft systems such as hydrogels and elastomers. Although the above-mentioned additive manufacturing (3D printing) techniques allow fabrication of channels within hydrogels or elastomers, these techniques require development of special materials and are not applicable to a wide range of materials. In addition, these conventional techniques require the use of excess material, which increases the cost of the fabrication. Accordingly, there still remains a need for a method of making 3D scaffolds and devices without the above drawbacks.

SUMMARY

The present disclosure avoids the drawbacks of conventional 3D printing methods and provides many other advantages. No additional steps are required. A reservoir of materials is eliminated. The present method not only eliminates the need of these items, but also allows direct printing of a matrix material and sacrificial material sequentially. The present method includes fabrication of polymeric scaffolds/devices with embedded structures using a novel extrusion based printing approach involving printing of the sacrificial polymer/hydrogel within the interface of the photocurable matrix layer, or vice versa. The printing may be sequential.

The present method utilizes a photo-curable solution of matrix polymer material (e.g., cell-laden hydrogel). Matrix polymer material refers to the material that comprises the main scaffold or device. Also utilized is a sacrificial polymer/hydrogel that refers to a polymer/hydrogel that can be removed after printing, for instance via dissolution in an aqueous solution. Also utilized is an extrusion-based printer system, which allows extrusion of polymer solutions under applied pressure. A dual printing system is used to first print matrix material up to a certain thickness that may be determined by the user.

After each print layer, the matrix material is exposed to light to partially crosslink the printed layer. This allows self-supporting of the matrix material enabling printing of low viscous bioinks. Thus, in one embodiment, the method includes the step of sequential printing of a photocurable polymer solution and a sacrificial polymer solution, in which the sacrificial polymer solution is printed directly within the interface of a partially crosslinked and freshly printed photocurable layer. When needed or as determined by the operator, the sacrificial layer is printed directly within the freshly printed matrix polymer solution before light exposure of this particular layer. Depending on the implementation, the sacrificial layer may be 100-1000 microns depending on the desired channel size.

After printing of the sacrificial polymer light is exposed to partially cross-link the sacrificial polymer layer, and a new layer of matrix material is printed. This process is repeated as needed. Scaffolds/devices may be created in human scale. There is no limit in total device thickness in the current approach. After the printing is done, the system is exposed to light (for example 4 minutes, but exposure time can differ for different materials) to fully crosslink the printed device/scaffold. Then the scaffold/device is immersed in an aqueous solution (such as phosphate buffer solution, PBS) to remove the sacrificial polymer, which will lead to formation of channels.

For easy handling of the scaffold/device, the printing could be done on a surface modified glass slide or microscope cover slip. Surface modification is done using 3-(trimethoxysilyl)propyl methacrylate that allows covalent cross linking of the matrix polymer to the glass slide. Sequential printing or printing of the sacrificial polymer within the interface of the printed matrix material allows formation of channels never before achievable by conventional methods.

In one embodiment, an extrusion-based printer system is disclosed, which allows extrusion of polymer solutions under applied pressure. Dual printing is used to first print matrix material up to a certain thickness as determined by the user. Again after each print layer, the material is exposed to light to partially crosslink the printed layer. This allows self-supporting of the matrix material.

Furthermore, the present method and system does not require a shear thinning material unlike conventional 3D printing methodologies. The needle used in the 3D printing of layers is only within the previously printed interface layer so the material doesn't require shear thinning behavior for needle to move freely. This feature of the present disclosure provides a significant improvement over current 3D printing methodologies and allows the use of almost any photocurable material as a matrix material.

The above objects and advantages are met by the presently disclosed method and apparatus. In addition the above and yet other objects and advantages of the present invention will become apparent from the hereinafter-set forth Brief Description of the Drawings, Detailed Description of the Invention, and claims appended herewith. These features and other features are described and shown in the following drawings and detailed description.

Furthermore, any combination and/or permutation of the embodiments are envisioned. For instance, it is possible to print the cell-laden matrix hydrogel with a sacrificial (or support) hydrogel by simply switching the order of the printing process. Or it is possible to print the matrix hydrogel with a support hydrogel first, and print the cells (e.g., aggregates or spheroids) directly with the freshly printed matrix hydrogel. Again, other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

To assist those of skill in the art in making and using the disclosed method to make a device using 3D printing and associated systems and methods, reference is made to the accompanying figures, wherein:

(FIGS. 3A-D) Pictures showing the printed scaffolds after removal of the sacrificial regions: (FIG. 3A) channels with varying channel diameter, (FIG. 3B) two-layer channel structure (channels are in different planes), (FIG. 3C) interconnected elliptical channels, and (FIG. 3D) channels forming NJIT. Coarse channels (500 μm in diameter) are printed for visual clarity and easy access with a regular size needle, but 100 μm channels can be printed;

DETAILED DESCRIPTION

Figure 1:
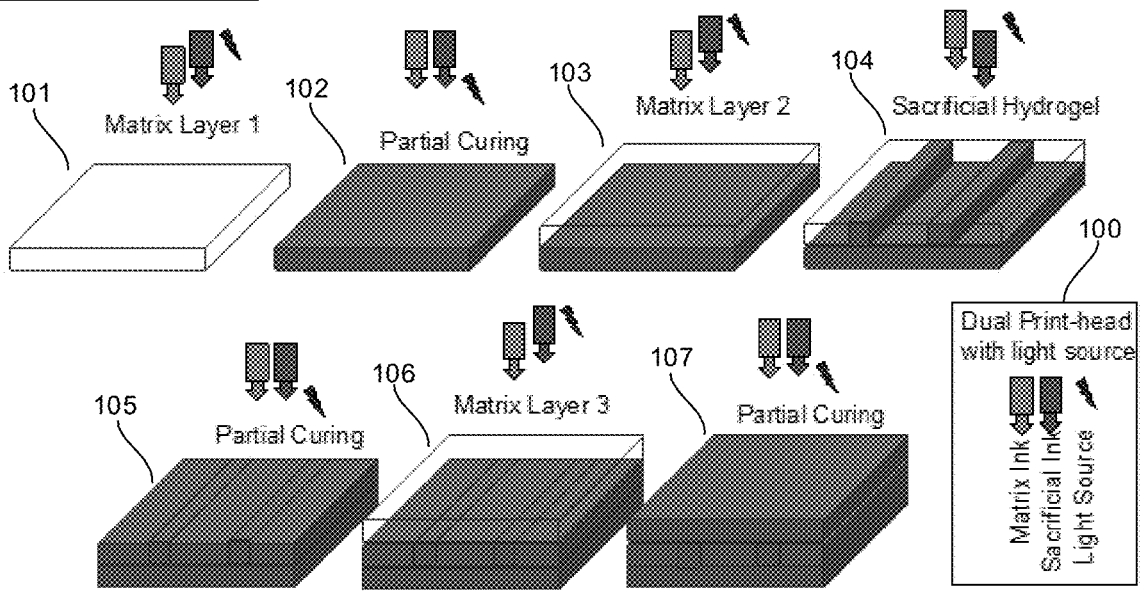
FIG. 1 shows views outlining a printing method to create a channel embedded in a 3D hydrogel, in accordance with one embodiment of the present disclosure.

Vascularization is a major limitation for development of human-scale functional tissues or organs. Fundamentally it requires ability to create channels within 3D soft scaffolds that mimics human tissue. Creating well defined channels within 3D hydrogels and/or elastomers are also important for development of soft devices towards organ-on-a-chip systems, such as but not limited to 3D tissue/disease models, to detect disease or screen for drugs. The present disclosure addresses this major gap in creating channels within soft 3D polymeric systems using additive manufacturing. Although additive manufacturing is utilized to create channels previously, this present novel approach eliminates the use of specially designed printers, specialty shear thinning material, the requirement for multiple steps, and the use of excess materials. This new approach is suitable for any photocurable hydrogel and elastomer formulation with the use of a sacrificial polymer ink such as polymers or hydrogels that are soluble in an aqueous media.

Exemplary embodiments are directed to 3D printing of soft polymeric scaffolds or devices. It should be understood that embodiments can generally be applied to other scaffolds or devices.

In one embodiment, a method is disclosed for 3D printing of soft polymeric (hydrogel or elastomer) scaffolds or devices with embedded channels with tunable shape and size (i.e., channel inner diameter). The method utilizes extrusion based printing of polymer solutions usually referred as direct ink writing (DIW) or BioPlotting, and requires sequential printing of a photocurable polymer solution referred herein as the matrix material, and a sacrificial polymer solution, i.e., preferable to dissolve in an aqueous media such as phosphate buffer saline (PBS).

In this embodiment, the fabrication process starts with 3D printing several layers of matrix material. Matrix material could be any photocurable hydrogel ink. The ink is not required to self-support itself after printing, which allows the use of a wide range of materials. After printing of each layer, the printed matrix solution is exposed to light for a very short time (~10 s) to partially cure the printed layer. This allows the matrix hydrogel to self-support itself. When the desired matrix material height (thickness) is reached, one additional layer of matrix material is printed but not exposed to light. The sacrificial material is directly printed within this matrix layer. This uncrosslinked matrix layer supports the printed sacrificial polymer/hydrogel. The system is then exposed to light to partially crosslink the matrix layer. Then another layer of matrix material is printed followed by light exposure. This process is repeated as needed to reach the final desired scaffold/device thickness.

The 3D printed construct is exposed to light to fully crosslink the matrix polymer, such as a hydrogel or elastomer, and immersed in an aqueous media to dissolve the sacrificial polymer or hydrogel. Dissolution of the sacrificial polymer/hydrogel leads to channel formation within the matrix hydrogel or elastomer. This method allows creation of channels within multiple print layers (different regions within z-axis) by printing the sacrificial polymer/hydrogel at the desired print layers (heights).

FIG. 1 shows views outlining one embodiment of a printing method. The method involves 3D printing several layers of matrix material. A dual print-head with light source 100 is utilized in the method. The reference numeral 100 comprises a matrix ink print-head, a sacrificial ink print-head and a light source as shown in FIG. 1. The portion of reference numeral 100 (matrix ink print-head, sacrificial ink print-head, and/or light source) that is closest to the shown layer indicates what portion is being utilized at that time during the method. A first matrix layer 101 is printed using a matrix ink and partially cured for a certain period of time to form a partially cured matrix layer 102. In one embodiment, the first matrix layer is partially cured using a light source for around 10 seconds. The partial curing time could vary depending on several factors, such as the material. A second matrix layer 103 is printed on the first matrix layer, which has been partially cured. A sacrificial material 104, such as a polymer or hydrogel, is printed using sacrificial ink within the second matrix layer. In one embodiment, the sacrificial material is printed within the second matrix layer before the second matrix layer is exposed to light. The second matrix layer is sized to support the sacrificial material. The first matrix layer, the second matrix layer, and/or the sacrificial material are partially cured as shown in 105 for a certain period of time to crosslink the second matrix layer. In one embodiment, only the second matrix layer is exposed to light in this step. A third matrix layer 106 is printed on the second matrix layer. The first matrix layer, the second matrix layer, the sacrificial material, and/or the third matrix layer are partially cured as shown in 107 for a certain period of time to crosslink the third matrix layer. In one embodiment, only the third matrix layer is exposed to light in this step.

A 3D printed construct is formed, which includes the first matrix layer, the second matrix layer, the sacrificial material, and the third matrix layer in this embodiment. While only three matrix layers and one sacrificial layer are shown in FIG. 1, the number of matrix layers and sacrificial layers could vary depending on the embodiment.

Figure 2:
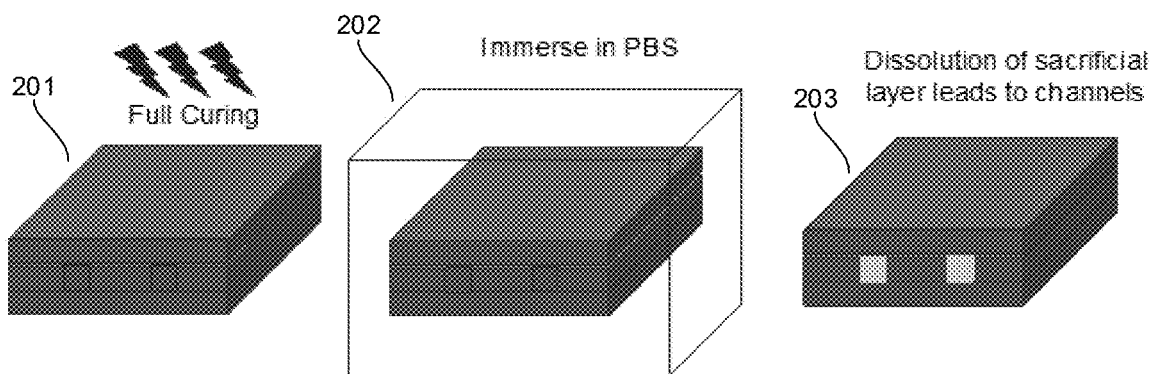
FIG. 2 shows views outlining one embodiment of a post-printing method to fully crosslink the matrix hydrogel and dissolve the sacrificial hydrogel to create channels.

FIG. 2 are views outlining one embodiment of a post-printing method. The method involves curing of the 3D printed construct to crosslink the matrix polymer for a certain period of time. In one embodiment, the 3D printed construct is fully cured as shown in step 201 using a light source, and depending on the implementation, the time of cure is for around 4 minutes. The curing time could vary depending on several factors, such as the material. The 3D printed construct is then immersed as shown in step 202 in an aqueous media to dissolve the sacrificial polymer or hydrogel. Depending on the embodiment, any aqueous media could be used, such as PBS. The duration of immersion is determined by the sacrificial material. In this particular case, the construct was immersed in PBS for 30 minutes at room temperature. It is possible to reduce this time significantly (about 5 min) when immersed at 4° C. Dissolution of the sacrificial layer leads to channels as shown in step 203. While only two channels are shown in FIG. 2, depending on the embodiment that the number of channels could vary.

The materials and the methods of the present disclosure used in one embodiment for a hydrogel scaffold and device will be described below. While the embodiment discusses the use of specific compounds and materials, it is understood that the present disclosure could employ other suitable materials. Similar quantities or measurements may be substituted without altering the method embodied below.

Methacrylated hyaluronic acid (MeHA) and alginate (MeAlg) MeHA hydrogels were used as matrix bioinks. These polymers were synthesized as described previously. Ink formulations were prepared by dissolving MeAlg (or MeHA) in PBS at different concentrations in the presence of a photoinitiator, lithium phenyl-2,4,6-trimethylbenzoylphosphinate (LAP), for blue light crosslinking. A blue light initiator was used as the 3D printer has a built in blue light source. Several ink formulations were developed by varying the MeAlg (or MeHA) concentration. One of the suitable bioink formulations was 9 wt. % MeHA, allowing extrusion based printing of the solution. The present inventors were able to generate struts (individual lines) as small as 100-microns in diameter.

Pluronic® (F-127), a common sacrificial bioink, was used as a sacrificial hydrogel, to create channels within matrix hydrogels. For this purpose, a dual head bioplotter was used to print the sacrificial and matrix bioink (MeHA) sequentially, as described in FIG. 1. For both matrix materials, the present inventors found that the partial curing time of 10 seconds was sufficient to create self-supporting printed structures. To create channels, sacrificial hydrogel was directly printed within the freshly printed matrix hydrogel layer as described in FIG. 1. After printing was completed, the scaffold was further crosslinked for 4 minutes. The scaffold was then immersed in PBS to dissolve the Pluronic gel. The scaffold was removed from the petri dish, and the PBS in the channels was removed by applying a gentle vacuum. PBS with red food coloring was then injected into each channel using a needle (34- to 27-gauge needle).

The approach is versatile and enables development of complex channels with tunable shape and size within photocurable hydrogels, either individual or interconnected. FIGS. 3A-3D and FIGS. 4A-4C demonstrate some of the 3D designs and corresponding 3D printed structures.

Figures 3A, 3B, 3C, 3D:
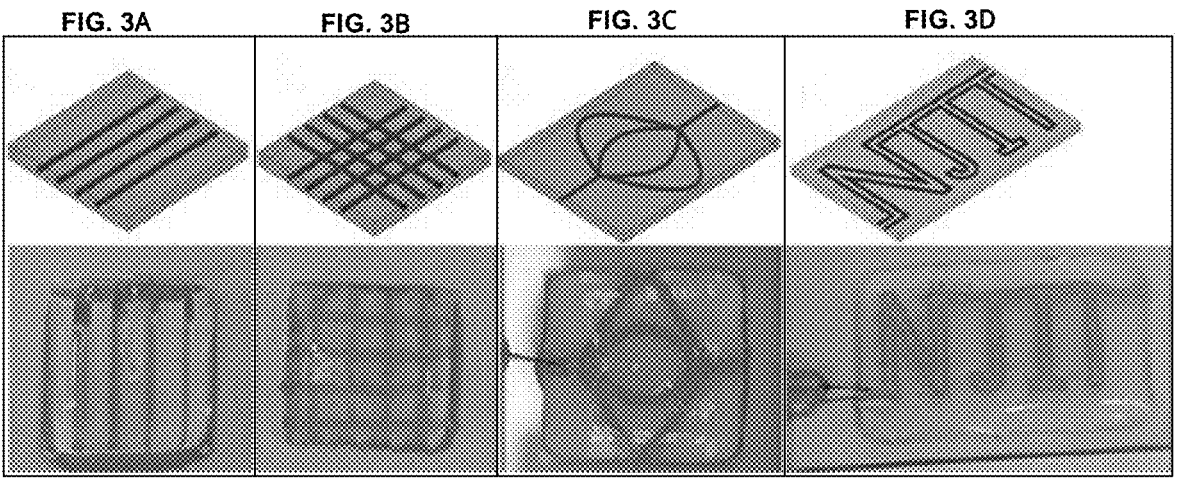
FIGS. 3A-3D show 3D design, and specifically (Top Row) CAD designs of the hydrogel scaffolds with channels (light gray: matrix; dark gray: sacrificial).

As shown in FIGS. 3A-3D a 3D design is accomplished. In particular for this embodiment is CAD designs of the hydrogel scaffolds with channels (light gray: matrix; dark gray: sacrificial). FIGS. 3A-3D are pictorial representations showing the printed scaffolds after removal of the sacrificial regions. FIG. 3A illustrates a plurality of channels with varying channel diameter. Depending on the implementation the diameter of the channels may all be the same or may be varied as represented in this figure. FIG. 3B shows two-layer channel structure where channels are in different planes. FIG. 3C illustrates a plurality of interconnected elliptical channels. Depending on the implementation the channels may be different geometrical shapes or all the same shape. FIG. 3D shows channels forming the logo NJIT. Coarse channels (500 μm in diameter) are printed for visual clarity and easy access with a regular size needle, but 100 μm channels can be printed depending on the embodiment.

Figures 4A, 4B, 4C:
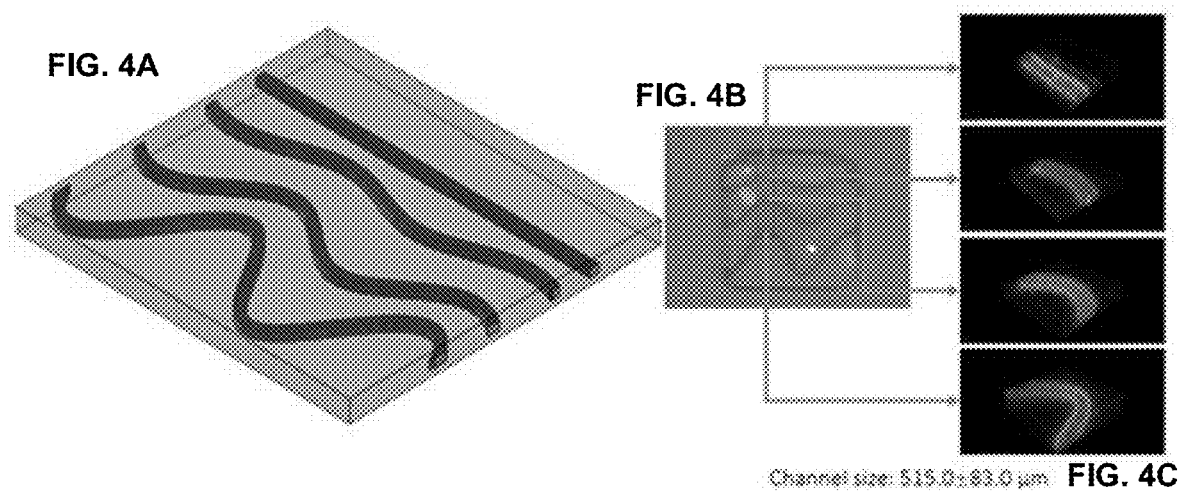
FIGS. 4A-4C show 3D printed structures, and feasibility studies showing (Left FIG. 4A) a schematic of a channel design, and (Center FIG. 4B) a top view of an actual sample having the channel design of FIG. 4A; 3D printed construct with Pluronic doped with red food coloring; and (Right FIG. 4C) confocal images of the channels in FIG. 4B taken at within the region of the black rectangle in Right and perfused with methacrylated rhodamine containing PBS, wherein the channels are smooth and cylindrical in shape with width equal to ~500 μm and scale bars are 500 μm.

FIGS. 4A-4C show 3D printed structures, and feasibility studies. As shown in FIG. 4A, a schematic of a channel design is illustrated. The channels may follow the same pathway or form various pathways as shown in this figure. FIG. 4B is a top view of an actual sample having the channel design of FIG. 4A. FIG. 4B is a 3D printed construct with Pluronic doped with red food coloring. FIG. 4C illustrates confocal images of the channels in FIG. 4B taken at within the region of the black rectangle in FIG. 4B and perfused with methacrylated rhodamine containing PBS, wherein the channels are smooth and cylindrical in shape with width equal to about 500 μm.

Figure 5:
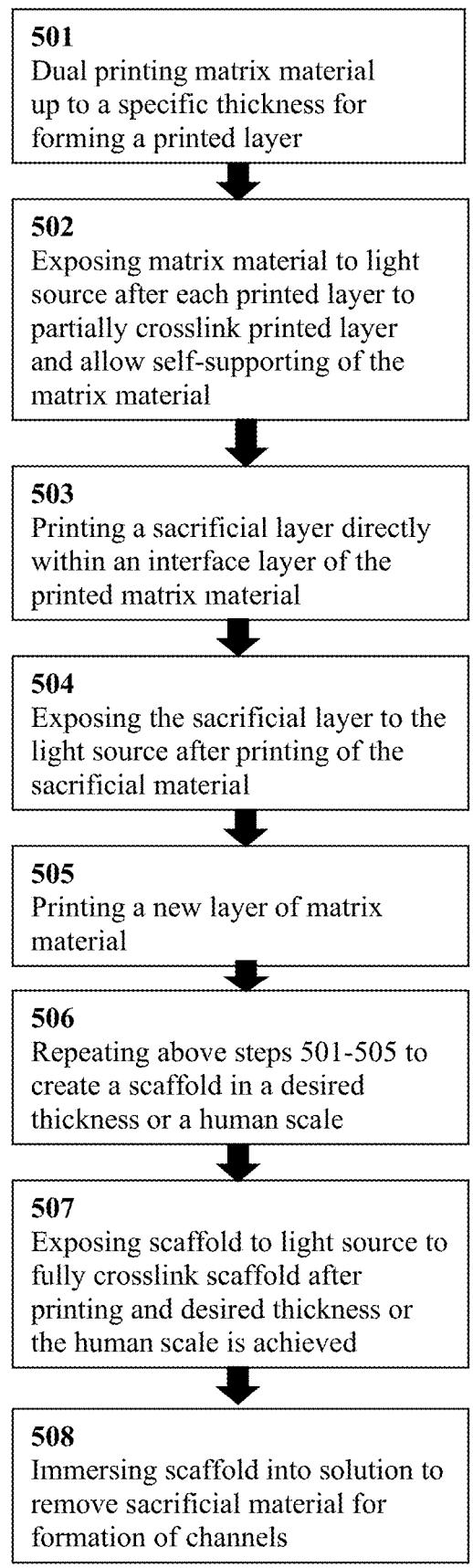
FIG. 5 shows a flow chart to create a channel embedded in a 3D structure, in accordance with one embodiment of the present disclosure.

FIG. 5 is a flow chart illustrating steps of one embodiment of the present method. Shown is one method for making a 3D scaffold. Step 501 illustrates dual printing a matrix material up to a specific thickness for forming a printed layer. Step 502 shows exposing the matrix material to a light source after each printed layer, and partially crosslinking the printed layer to allow self-supporting of the matrix material. As shown in Step 503, printing a sacrificial layer with a sacrificial material directly within an interface layer of the printed matrix material is accomplished. Step 504 illustrates exposing the sacrificial layer to the light source after printing of the sacrificial material. Step 505 illustrates printing a new layer of matrix material. Step 506 shows how repeating the above first through fifth steps (501-505) may be done to create a scaffold in a desired thickness or a human scale. Step 507 illustrates exposing the scaffold to the light source to fully crosslink the scaffold after printing and the desired thickness or the human scale is achieved. In Step 508, it is shown that immersing the scaffold into an aqueous solution is done to remove the sacrificial material for a formation of channels.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

What is claimed is:

1. A method for making a 3D scaffold or a device, comprises:
    printing an uncured photocurable polymer matrix material layer and a sacrificial polymer material layer; and
    wherein the sacrificial polymer material layer is printed directly within the uncured photocurable polymer matrix material layer before the photocurable polymer matrix material layer is cured by exposure to light; wherein the uncured photocurable matrix material layer is a bio ink;
    forming a plurality of embedded channels for vascularization, wherein the embedded channels have either a same diameter or a varied diameter; and performing the following steps:
    (i) dual printing the uncured matrix material up to a specific thickness for forming a printed layer for the printing of the photocurable polymer matrix material layer;
    (ii) exposing the matrix material to a light source after each of the printed layer, and partially crosslinking the uncured matrix material layer to form a partial crosslinking layer to allow self-supporting of the matrix material;
    (iii) printing a second uncured matrix material layer on top of the partial crosslinking layer;
    (iv) printing the sacrificial layer with a sacrificial material within the second uncured matrix material layer;
    (v) exposing the partial crosslinking layer and the second uncured matrix material layer to the light source after printing of the sacrificial material inside the second uncured matrix material layer;
    (vi) printing a new layer of uncured matrix material on top of the second uncured matrix material layer that is now cured;
    repeating above (i) through (vi) steps to create a vascular scaffold in a desired thickness;
    exposing the scaffold to the light source to fully crosslink the scaffold after printing and the desired thickness is achieved; and
    immersing the scaffold into an aqueous solution to remove the sacrificial material for the formation of the plurality of embedded channels.

2. The method of claim 1 further comprises: placing an extrusion needle only within the uncured photocurable matrix material layer for free motion movement of the needle without using a shear thinning matrix material; and wherein the printing of the photocurable polymer matrix material layer and the sacrificial polymer material layer is done using partial curing.

3. The method of claim 2, wherein the sacrificial layer is 100-1000 microns in diameter for forming the plurality of embedded channels within the matrix layer, and wherein the embedded channels are either connected or not connected.

4. The method of claim 1, wherein the printing further comprises creating a vascularized scaffold in a single step using dual extrusion printing.

5. The method of claim 4, wherein the vascularized scaffold is a hydrogel with the plurality of embedded channels for vascularization, and the embedded channels having either the same diameter or the varied diameter within a range of about 100 μm-500 μm.

6. The method of claim 4, wherein the vascularized scaffold is a microfluidic device made from an elastomer or a hydrogel.

7. The method of claim 1, wherein the printing the sacrificial layer further comprises placing an extrusion needle only directly within the uncured matrix material layer for a free motion movement of the needle without using shear thinning behavior material in the uncured matrix material layer.

8. The method of claim 1, wherein the dual printing utilizes an extrusion-based printer system that allows extrusion of polymer materials or solutions under applied pressure.

9. The method of claim 1, wherein the fabrication of channels is embedded in a hydrogel.

10. The method of claim 9, wherein the dual printing is a reservoir-free printing with no supportive hydrogel reservoir.

11. A method for making a 3D scaffold or a device, comprises:
   printing a photocurable polymer matrix material layer and a sacrificial polymer material layer; and wherein the photocurable matrix material layer is an uncured bio ink and has printed directly within it the sacrificial polymer material layer; and
   wherein the sacrificial polymer material layer is the bio ink used as a sacrificial hydrogel; and
   forming a plurality of embedded channels directly within the matrix material layer; and wherein the embedded channels are a multi-layer channel structure wherein the embedded channels are in a different plane or a same plane; and performing the following steps:
   (i) dual printing the uncured matrix material up to a specific thickness for forming a printed layer for the printing of the photocurable polymer matrix material layer;
   (ii) exposing the matrix material to a light source after each of the printed layer, and partially crosslinking the uncured matrix material layer to form a partial crosslinking layer to allow self-supporting of the matrix material;
   (iii) printing a second uncured matrix material layer on top of the partial crosslinking layer;
   (iv) printing the sacrificial layer with a sacrificial material within the second uncured matrix material layer;
   (v) exposing the partial crosslinking layer and the second uncured matrix material layer to the light source after printing of the sacrificial material inside the second uncured matrix material layer;
   (vi) printing a new layer of uncured matrix material on top of the second uncured matrix material layer that is now cured;
   repeating above (i) through (vi) steps to create a vascular scaffold in a desired thickness;
   exposing the scaffold to the light source to fully crosslink the scaffold after printing and the desired thickness is achieved; and
   immersing the scaffold into an aqueous solution to remove the sacrificial material for the formation of the plurality of embedded channels.

12. The method of claim 11, wherein the bio ink is a cell-laden hydrogel ink.

13. The method of claim 11, wherein the formation of the plurality of channels further includes forming the plurality of channels with varying channel diameter, and varying shape embedded channels within the matrix material layer.

14. The method of claim 11, wherein methacrylated hyaluronic acid (MeHA) or methacrylated alginate (MeAlg) hydrogels is used as the bio ink.

15. The method of claim 14, wherein the methacrylated hyaluronic acid (MeHA) is 9 wt. %.

16. A method for making a 3D scaffold or a device, comprises:
   printing an uncured photocurable polymer matrix material layer and a sacrificial polymer material layer; and
   wherein the sacrificial polymer material layer is printed directly within the uncured photocurable polymer matrix material layer before the photocurable polymer matrix material layer is cured by exposure to light;
   wherein the uncured photocurable matrix material layer is a bio ink;
   forming a plurality of embedded channels for vascularization, wherein the embedded channels have either a same diameter or a varied diameter; and performing the following steps:
   (i) printing the uncured matrix material up to a specific thickness for forming a printed layer for the printing of the photocurable polymer matrix material layer;
   (ii) exposing the matrix material to a light source after each of the printed layer, and partially crosslinking the uncured matrix material layer to form a partial crosslinking layer to allow self-supporting of the matrix material;
   (iii) printing a second uncured matrix material layer on top of the partial crosslinking layer;
   (iv) printing the sacrificial layer with a sacrificial material within the second uncured matrix material layer;
   (v) exposing the partial crosslinking layer and the second uncured matrix material layer to the light source after printing of the sacrificial material inside the second uncured matrix material layer;
   (vi) printing a new layer of uncured matrix material on top of the second uncured matrix material layer that is now cured;
   repeating above (i) through (vi) steps to create a vascular scaffold in a desired thickness;
   exposing the scaffold to the light source to fully crosslink the scaffold after printing and the desired thickness is achieved; and
   immersing the scaffold into an aqueous solution to remove the sacrificial material for the formation of the plurality of embedded channels.

* * * * *